United States Patent [19]

Hayward

[11] Patent Number: 4,721,796

[45] Date of Patent: Jan. 26, 1988

[54] NITRATES OF D-ISOIDIDE

[76] Inventor: Lloyl D. Hayward, 2041 West 29th Avenue, Vancouver, British Columbia V6J 2Z9, Canada

[21] Appl. No.: 931,904

[22] Filed: Nov. 14, 1986

Related U.S. Application Data

[63] Continuation of Ser. No. 635,277, Jul. 27, 1984, abandoned.

[30] Foreign Application Priority Data

Aug. 5, 1983 [CA] Canada ................................ 434018

[51] Int. Cl.$^4$ .......................................... C07D 493/04
[52] U.S. Cl. .................................................. 549/464
[58] Field of Search ......................................... 549/464

[56] References Cited

U.S. PATENT DOCUMENTS 3,454,603  7/1969  Hartman ............................. 549/464

FOREIGN PATENT DOCUMENTS 885977  11/1971  Canada .

OTHER PUBLICATIONS

Tipson et al., Carbohydrate Research, vol. 7, pp. 232–243 (1968).
Boghert et al., Naunyn–Schmiedeberg's Arch., Pharmacol., vol. 275, pp. 339–342 (1972).
Halliday et al., J. Pharm. Pharmacol. vol. 17, No. 5, pp. 309–314 (Discussion pp. 314–315) (1965).
Fletcher, Jr. et al., JHCS, 68, pp. 939–941 (1946).
Hicks et al., Can. J. Chem, 52, pp. 3367–3372 (1974).
Wiggins, J. Chem. Soc., pp. 1403–1405 (1947).
Jackson et al., Can. J. Chem., 37, pp. 1048–1052, (1959).

*Primary Examiner*—Richard A. Schwartz
*Assistant Examiner*—Bernard I. Dentz
*Attorney, Agent, or Firm*—Brooks Haidt Haffner & Delahunty

[57] ABSTRACT

Nitrate esters of D-isoidide which are useful as cardiovascular agents, and crystalline D-isoidide from which such nitrates are derivable.

3 Claims, No Drawings

NITRATES OF D-ISOIDIDE

This application is a continuation of application Ser. No. 635,277, filed July 27, 1984, now abandoned.

This invention relates to new cardiovascular agents and to a process for their preparation. In particular, the invention provides new chemical compositions, the mono and dinitrate esters of D-isoidide (1,4:3,6 dianhydro-D-iditol), which have activity useful in the treatment of cardiovascular disorders and in particular, as vasodilators. The invention also provides a process for the recovery of the D-isoidide precursor as a crystalline substance, facilitating the manufacture of such new chemical compositions.

The new nitrate esters of this invention are optical isomers of known compounds which also possess substantial biological activity. In particular, compositions of this invention, such as D-isoidide dinitrate are indicated in control of angina pectoris, coronary vasodilation, coronary vasospasm, limitation in size of myocardiac infarction, improved cardiac hemodynamics, hypertension, esophageal spasm; biliary spasm and glaucoma. These compositions can be administered in a variety of dosage forms suitable for oral, including the sublingual and chewable routes, parenteral, transdermal, nasal and spray administration.

Although L-isoidide and its mono, and dinitrate have long been known [Jackson and Hayward, Can. J. Chem. 37, 1048–1052 (1959)], and although the precursor D-isoidide has heretofore been prepared in impure mixtures, the mono- and dinitrates of D-isoidide have not heretofore been prepared. The D-compounds of this invention, while identical to their known optical isomers in physical properties, possess significantly different biological activity since they are structurally derived from compounds which do not occur in nature. In particular, it is anticipated that the D-compounds of this invention are free of certain adverse reactions which characterize similar known compounds, such as the tendency to cause headaches.

Although the D-isoidide precursor has been known to exist in the impure state, it is also a particular object of this invention to provide a process for its recovery in crystalline form.

Generally, in accordance with this invention, crystalline D-isoidide is prepared from crude mixtures of the compound by preparation of the dibenzoate ester which is crystallized to recover it from the crude mixtures and then hydrolyzed, followed by separation of benzoic acid and recovery of crystals of the desired D-isoidide.

D-isoidide can suitably be prepared, first by following the procedure of Tipson and Cohen [Carbohyd. Res. 7, 232–243 (1968) to prepare the 1,2:5,6-di-O-isopropylidine-di-O-p-toluenesulfonyl-D-mannitol (DIPMDT). In this procedure, the starting material is D-mannitol which is readily available. The D-mannitol is condensed with acetone to block the 1,2,5 and 6 carbon atoms forming 1,2:5,6 di-O-isopropylidine-D-mannitol (DIIPM).

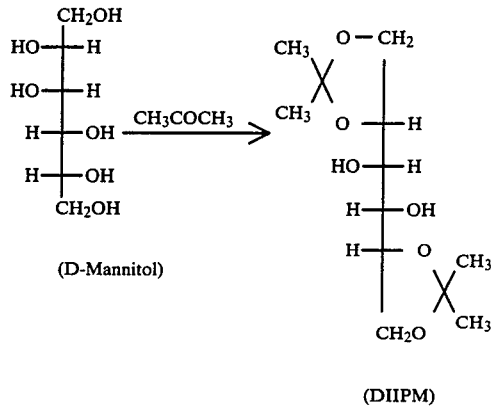

Still following the Tipson and Cohen procedure, the DIIPM is tosylated at the 3 and 4 positions to provide leaving groups, which in accordance with the literature upon anhydroring formation and hydrolysis, should result in inversion to the D-iditol configuration.

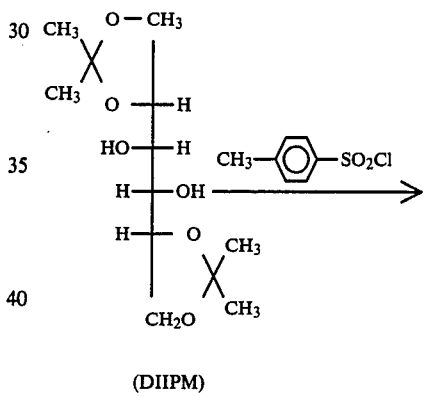

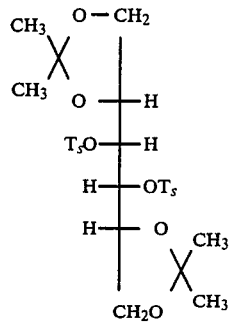

The 3,4-ditosylate is then converted to crude D-isodide by acid hydrolysis followed by neutralization of the acid to prepare the D-isoidide in a crude mixture from which efforts to separate the D-isoidide have been fruitless.

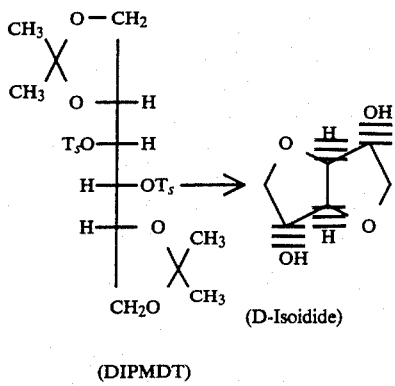

(DIPMDT)    (D-Isoidide)

In accordance with this invention, the crude mixture containing D-isoidide is treated to form the dibenzoate which can be recovered in crystalline form separating it from sodium tosylate and other impurities which had prevented the crystallization of the D-isoidide. The D-isoidide dibenzoate is then hydrolyzed with alkali to separate benzoic acid leaving an aqueous solution of the D-isoidide from which the crystalline D-isoidide is readily recovered. The mono- and dinitrate esters of D-isoidide are then prepared following the techniques described in Jackson and Hayward, supra, for preparing dianhydrohexitol dinitrates.

EXAMPLE 1

Preparation of 1,2:5,6-di-O-isopropylidine-D-mannitol (DIIPM)

291 grams of zinc chloride was dissolved in 1470 ml. of acetone, and the resultant solution was filtered. 150.4 grams of D-mannitol was added, and the reaction mixture was heated until the mannitol dissolved. The solution was treated with 363 grams of potassium carbonate dissolved in 363 ml. of water and allowed to stand overnight. Undissolved solids were filtered off, and the remaining liquid was evaporated to dryness, yielding a waxy solid (net weight 180 grams) which was then dissolved in 180 ml. of chloroform. 1050 ml. of heptane was added to the solution; charcoal was added; and the solution was hot filtered and left to crystallize overnight. The solids were recovered by suction filtration as dry as possible and then further dried in an oven at 50° C. yielding 68 grams DIIPM (31.4% yield, m.p. 110°–115° C.).

EXAMPLE 2

Preparation of 1,2:5,6-O-isopropylidine-3,4-di-O p-toluenesulfonyl-D-mannitol (DIPMDT)

The 68 grams of DIIPM prepared in Example 1 was dissolved in 450 ml. of anhydrous pyridine. 110 grams of p-toluenesulfonyl chloride was then added. The mixture was heated slightly and allowed to stand in a warm area for one week. The solution was cooled with stirring on an ice bath to 0° C. 200 ml. of water was added in increments of 10 ml., 10 ml., 10 ml. 20 ml., 50 ml. and 100 ml. at 5 minute intervals, and then an additional 500 ml. of water was added. The reaction mixture was allowed to stand in a cold room for 2½ days. The solids formed were filtered off and dissolved in 300 ml. of chloroform. The mixture was then extracted twice with 50 ml. aliquots of 5% potassium bisulfate solution followed by two extractions with 100 ml. aliquots of 5% sodium bicarbonate solution. The chloroform mixture was then dried with sodium sulfate, filtered, and evaporated to give a crude yield of 111 grams of an oil smelling of pyridine. The oil was then dissolved in 550 ml. of boiling methanol, treated with charcoal, hot filtered and crystallized overnight in a cold room. The solid was filtered off, washed with methane and then dried at 30° C. for a 33.8% yield of DIPMDT (50.0 grams, m.p. 116°–119° C.). A second crop was collected in like manner to yield an additional 2 grams (m.p. 100°–105° C.).

EXAMPLE 3

Conversion to D-isoidide 20 grams of the DIPMDT of Example 2 was dissolved in 115 ml. of 1,4-dioxane. 55 ml. of water and 2.1 ml. of concentrated sulfuric acid were then added. The mixture was refluxed for three hours, cooled to room temperature, neutralized with 30 grams of sodium bicarbonate and allowed to stand overnight. The mixture was then filtered and evaporated to a paste. The paste was slurried in 98% ethyl acetate, filtered and left to evaporate.

EXAMPLE 4

Preparation of DIIPM 400 grams of zinc chloride was dissolved in 2020 ml. of acetone and filtered. 207 grams of D-mannitol was then dissolved in the solution, and the solution was cooled. 500 grams of potassium carbonate in 500 ml. of water was added, and the solution was left overnight. The solution was then filtered. The solid phase was extracted with chloroform; the filtrate was extracted with chloroform; and the extracts were combined, dried over sodium sulfate, filtered and evaporated to recover a waxy solid, wet weight 234 grams. 1400 ml. of heptane was added to the solid which was then boiled, hot filtered and allowed to cool overnight. The solid formed was suction filtered as dry as possible and then allowed to dry overnight with a yield of DIIPM of 123 grams (41.2% yield, m.p. 107°–112° C.).

EXAMPLE 5

Preparation of DIPMDT

The 123 grams of DIIPM prepared in Example 4 was dissolved in 815 ml. anhydrous pyridine, and 200 g. of p-toluene sulfonyl chloride was added. The mixture was swirled until the toluene sulfonyl chloride dissolved, and then was stoppered and allowed to stand in a warm place for two days. The solution was then cooled on an ice bath while water was added at 5 minute intervals and in increments of 20 ml., 20 ml., 20 ml., 40 ml., 40 ml., 100 ml., and 200 ml. The mixture was finally poured into one liter of water and allowed to stand in a cold room overnight. The resultant solids were filtered from the remaining solution and dissolved in methylene chloride. The methylene chloride solution was extracted eight times with 100 ml. aliquots of 5% potassium bisulphate and then twice with 100 ml. aliquots of 5% sodium bicarbonate. The methylene chloride was then dried with sodium sulfate, filtered, and evaporated to an oil which was crystallized from methanol with a yield of 44 g. of DIPMDT (16.4% yield, m.p. 115°–117° C.).

EXAMPLE 6

Conversion to D-Isoidide 40 grams of the DIPMDT prepared in Example 5, 230 ml. of 1,4-dioxane, 100 ml. of water and 14.2 ml. of concentrated sulfuric acid were placed in a flask and refluxed for three hours. The reaction mixture was cooled to room temperature, then neutralized with 60 g. of sodium bicarbonate and allowed to stand overnight. The resultant slurry was filtered, and the recovered solid washed with 1,4 dioxane and discarded. The filtrate was evaporated to a paste which was slurried in 1,4 dioxane, filtered through SuperCel and then evaporated to a cloudy oil.

EXAMPLE 7

Preparation of D-Isoidide dibenzoate (DIIDB)

The oil produced in Example 6 and the evaporated filtrate produced in Example 3 were combined in a flask with 100 ml. absolute ethanol and refluxed with charcoal for one hour. The mixture was then hot filtered through SuperCel and evaporated in an oil. (At this point the mixture still contained some sodium tosylate). The oil was slurried in 1,4-dioxane, filtered and evaporated to leave a dark clear oil which was refluxed in 50 ml. of absolute ethanol with charcoal for ½ hour. The mixture was then hot filtered through SuperCel and evaporated to an oil (17 .g.) which was dissolved in 135 ml. of anhydrous pyridine and then cooled to 5° C., stirring on an ice bath. 60 grams of benzoyl chloride was added slowly to the mixture, keeping the temperature at about 5° C. This took about two hours. The mixture was then refluxed for ½ hour, and 5 ml. of methanol was added to decompose any unreacted benzoyl chloride. The mixture was then allowed to cool in a cool room. The reaction mixture (with solid pyridinium chloride) was then diluted with 550 ml. of 5% sodium bicarbonate solution, a seed of dibenzoate was added, an oil formed, and the mixture was allowed to stand in a cold room to solidify the oil. The solution was then suction filtered to separate the solid material, which was sucked as dry as possible, and then the solid was recrystallized in 60 ml. of methanol and cooled in a cold room. Fine white crystals were filtered off in a first crop of 9.5 g. of DIIDB (m.p. 109°–110° C.). The mother liquor of the reaction mixture was extracted with 400 ml. of methylene chloride and the organic layer was dried with sodium sulfate and evaporated to yield an oil smelling of pyridine. The oil was poured into 500 ml. of water with approximately 10 g. of sodium bicarbonate dissolved in it. The oil-water mixture was then filtered and washed with water. About 5 g. of additional solid was isolated which was dissolved in the methanol mother liquor from the first crop of crystals. The combined solid and mother liquor mixture was boiled down to about 50 ml., and then hot filtered to remove insolubles. The solution was allowed to cool in a cold room and again crystals formed. The solid was separated by suction filtration and dried at about 40° C. for an additional yield of 3.0 g. of DIIDB, m.p. 102°–103° C.

EXAMPLE 8

Preparation of Crystalline D-isoidide 11.5 g. of DIIDB was refluxed in 150 ml. of methanol. 6 g. of sodium hydroxide in 66 ml. of water was added through the condenser, maintaining the reflux. The mixture refluxed a total of 6 hours, then was evaporated to about 150 ml. and poured into 16.5 ml. of concentrated hydrochloride acid in 60 ml. of water. Benzoic acid precipitated immediately, and the solution was allowed to cool overnight. The precipitated solid was then filtered off, washed with water and discarded. The filtrate was extracted with ethyl ether and evaporated to dryness. The resultant solid was slurried in methanol and reevaporated. The solid was then boiled in about 80 ml. of ethyl acetate and filtered. A further 40 ml. of ethyl acetate was used to reextract the remaining solid and combined with the first ethyl acetate extract. The combined extracts were then evaporated to about 20 ml., seeded and then cooled in a cold room. A copious solid precipitate appeared after about 30 minutes. The solid precipitate was separated by filtration, dried and yielded 3 grams of crystalline D-isoidide (m.p. 48°–50° C.).

EXAMPLE 9

Preparation of D-isoidide dinitrate (DIIDN)

3 g. of D-isoidide were dissolved in 22.5 ml. of 2:1 acetic acid; acetic anhydride. A solution was made up of 22.5 ml. of 1:1 acetic acid; acetic anhydride to which 7.5 ml. of fuming nitric acid was added, slowly with stirring to keep the temperature below 5° C. The nitrating solution was then added to the D-isoidide solution slowly with stirring to keep the temperature below 5° C. The solution was stirred at 4° C. for two hours and then was poured in 600 ml. of water at 0° C. and allowed to stand overnight. The solution was filtered, and about 2.5 gr. of a fluffy white solid was collected. This was boiled in 20 ml. of methane, treated with charcoal and hot filtered. On cooling the filtrate, long needle crystals were formed which were separated by filtration and dried under vacuum for a yield of 0.8 g. of DIDDN (m.p. 63°–66° C.). The D-isoidide dinitrate exhibited an IR spectrum matching that of L-isoidide dinitrate and had a specific rotation, $[\alpha]_d^{22.5}$ of $-97.6°$.

EXAMPLE 10

Preparation of the mononitrate ester of D-isoidide

The procedure of Example 9 is repeated except that the amount of nitrating solution is 2.5 ml. of the 1:1 acetic acid; acetic anhydride mixture to which 0.85 ml. of fuming nitric acid is added, and D-isoidide mononitrate is recovered by extracting the aqueous reaction mixture twice with ether after standing overnight. The ether extract is reduced under vacuum and then freeze dried to give the mononitrate ester (m.p. 18°–19° C.).

The nitrate esters of D-isoidide, as noted above, are useful as cardiovascular agents. In general, they are used similarly to the nitrate esters of, for example, D-isosorbide. For example, D-isoidide dinitrate is useful as a replacement for D-isosorbide dinitrate in essentially the same formulations and dosage levels as D-isosorbide dinitrate in the treatment of angina pectoris.

What is claimed is:
1. A nitrate ester of D-isoidide.
2. D-isoidide dinitrate.
3. D-Isoidide mononitrate.

* * * * *